• US005741288A

United States Patent [19]
Rife

[11] Patent Number: 5,741,288
[45] Date of Patent: Apr. 21, 1998

[54] RE-ARMABLE SINGLE-USER SAFETY FINGER STICK DEVICE HAVING RESET FOR MULTIPLE USE BY A SINGLE PATIENT

[75] Inventor: Douglas Earl Rife, Palo Alto, Calif.

[73] Assignee: Chemtrak, Inc., Sunnyvale, Calif.

[21] Appl. No.: 670,513

[22] Filed: Jun. 27, 1996

[51] Int. Cl.$^6$ ............................................. A61B 17/32
[52] U.S. Cl. ................................... 606/181; 606/181
[58] Field of Search .......................... 606/167, 181–182, 606/184–185, 189; 604/46–47, 136–137; 128/760, 763, 770

[56] References Cited

U.S. PATENT DOCUMENTS

| | | | |
|---|---|---|---|
| 4,449,529 | 5/1984 | Burns et al. | 128/314 |
| 4,539,988 | 9/1985 | Shirley et al. | 138/314 |
| 4,658,821 | 4/1987 | Chiodo et al. | 128/314 |
| 4,715,374 | 12/1987 | Maggio | 128/314 |
| 4,889,117 | 12/1989 | Stevens | 606/181 |
| 4,892,097 | 1/1990 | Ranaletta et al. | 606/182 |
| 4,976,724 | 12/1990 | Nieto et al. | 606/182 |
| 4,994,068 | 2/1991 | Hufnagle | 606/181 |
| 5,207,699 | 5/1993 | Coe | 606/182 |
| 5,304,192 | 4/1994 | Crouse | 606/181 |
| 5,314,441 | 5/1994 | Cusack et al. | 606/192 |
| 5,318,584 | 6/1994 | Lange et al. | 606/182 |
| 5,324,303 | 6/1994 | Strong et al. | 606/181 |
| 5,334,195 | 8/1994 | Gollobin | 606/131 |
| 5,366,469 | 11/1994 | Steg et al. | 606/182 |
| 5,395,388 | 3/1995 | Schraga | 606/182 |
| 5,421,357 | 6/1995 | Enström | 138/754 |
| 5,423,847 | 6/1995 | Strong et al. | 606/182 |
| 5,439,473 | 8/1995 | Jorgensen | 606/182 |
| 5,454,828 | 10/1995 | Schraga | 606/181 |
| 5,540,709 | 7/1996 | Ramel | 606/183 |
| 5,628,764 | 5/1997 | Schraga | 606/181 |

OTHER PUBLICATIONS

Incision Technologies brochure, "Tenderlett™ the tender touch for fingers" Rev. 7–91 (2 pages).

*Primary Examiner*—Michael Buiz
*Assistant Examiner*—Nancy Mulcare
*Attorney, Agent, or Firm*—Hana Verny

[57] ABSTRACT

A lancet or finger-stick device operable to make a small incision into the vascular tissue of the skin to induce a controllable blood flow is particularly suited for incisions of the finger-tip of a patient. The device and method provide multiple use by a single-user in that the device provides an autologous re-use feature, such that an individual can reset and reuse the device on the same patient in case of an accidental misfire prior to actual use or if the first incision does not provide a sufficient blood sample. A disabling mechanism which the individual performs immediately prior to disposal of the used device is incorporated into the invention. These features permit the user of a consumer self-test or professional-use test to re-stick an individual's fingertip in the event that the first try is unsuccessful or the blood flow is inadequate. It also insures sterility of the unused unit and provides enhanced safety since the device cannot be accidentally fired or reused by another individual after being disposed.

18 Claims, 11 Drawing Sheets

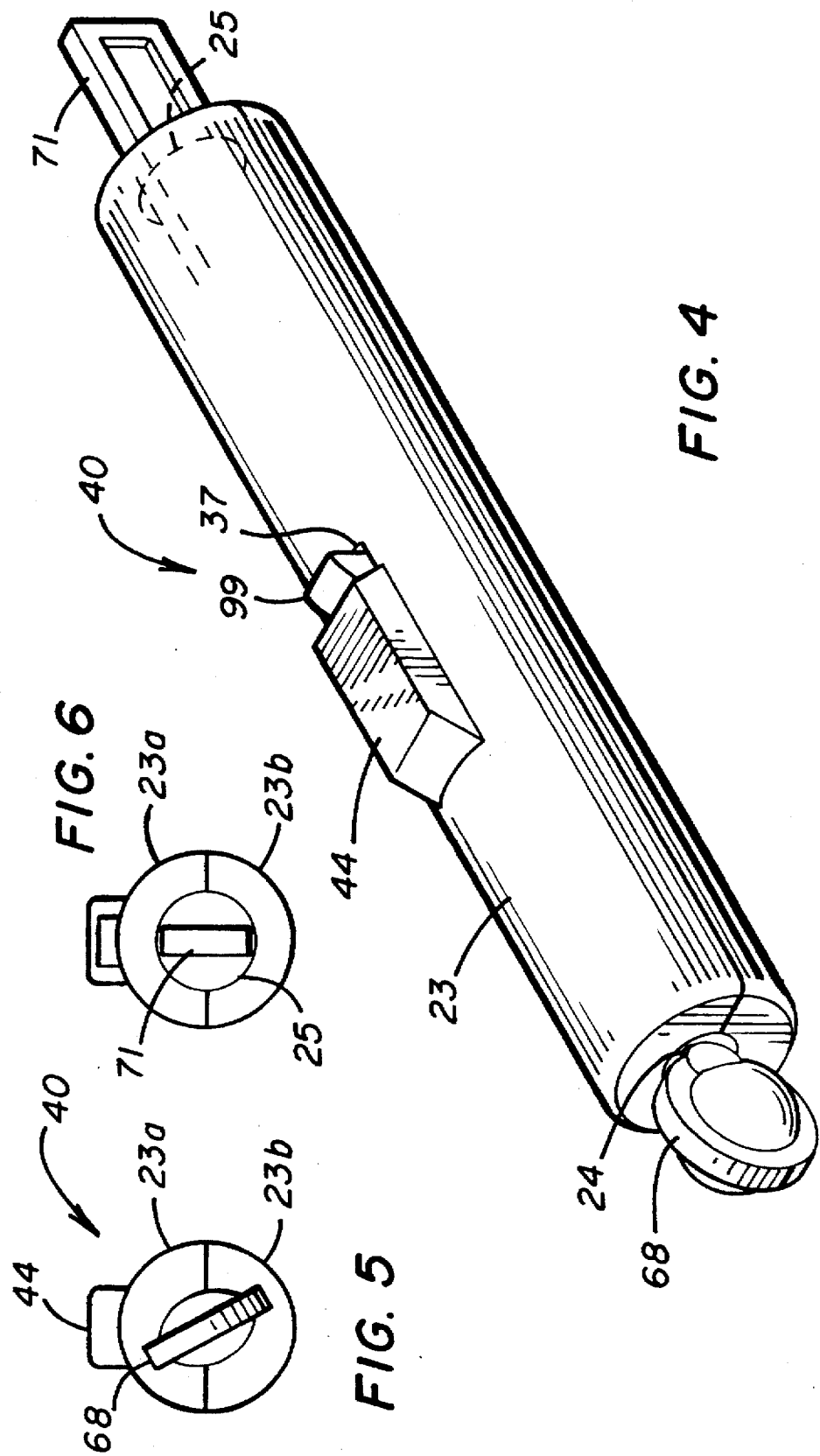

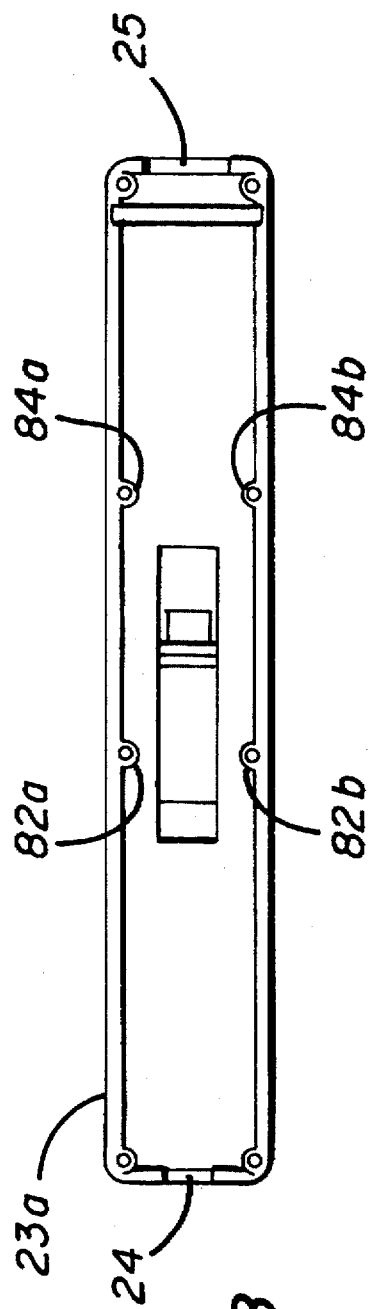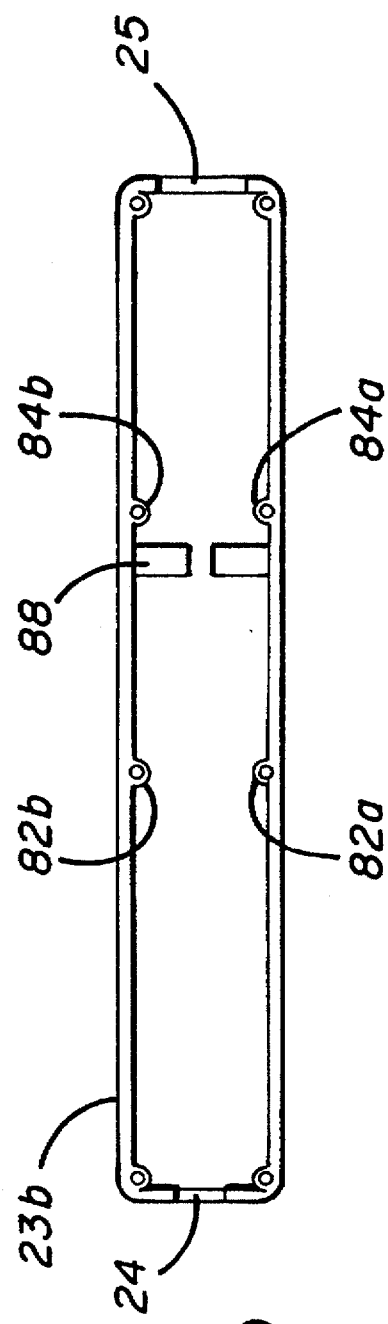

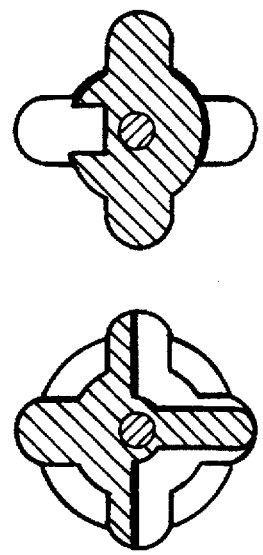
FIG. 13b
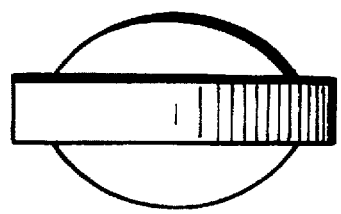
FIG. 13e
FIG. 13d
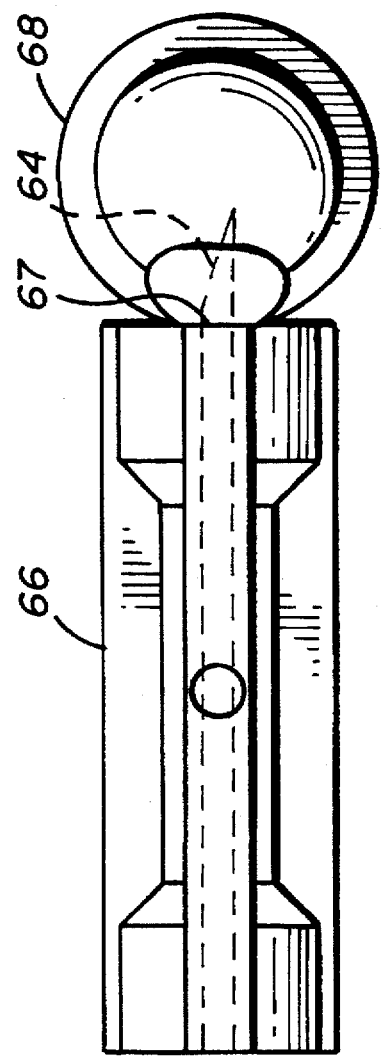
FIG. 13a (Prior Art)
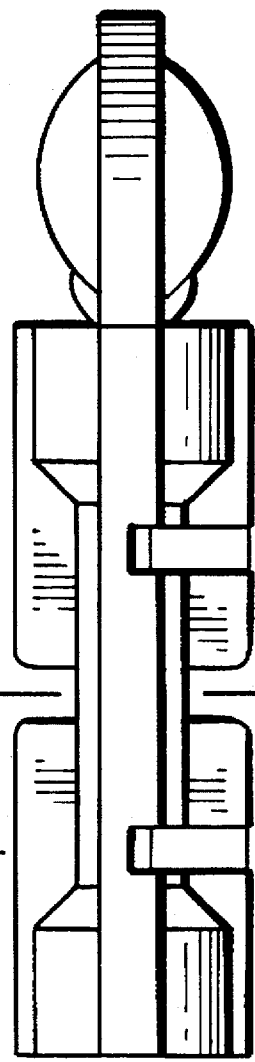
FIG. 13c

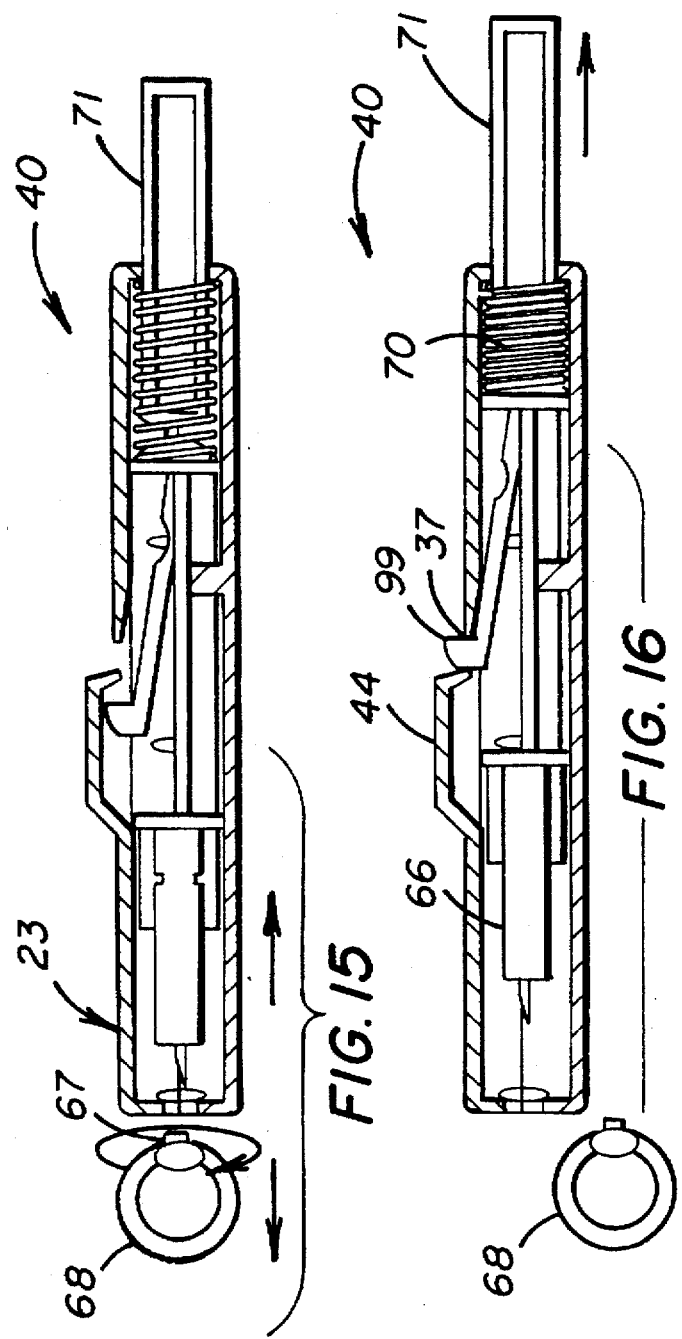

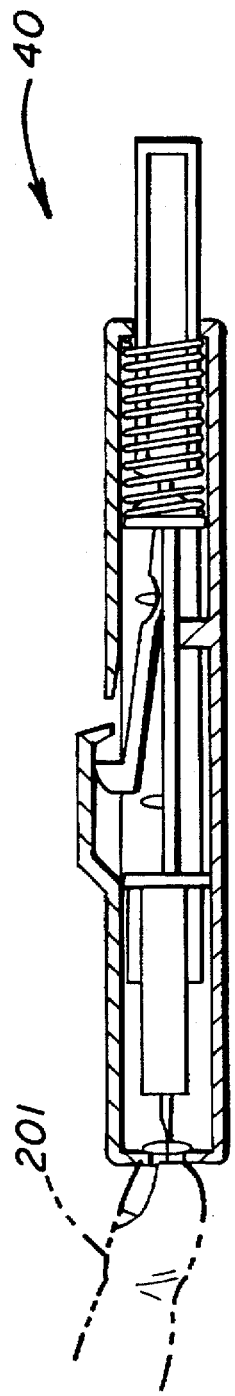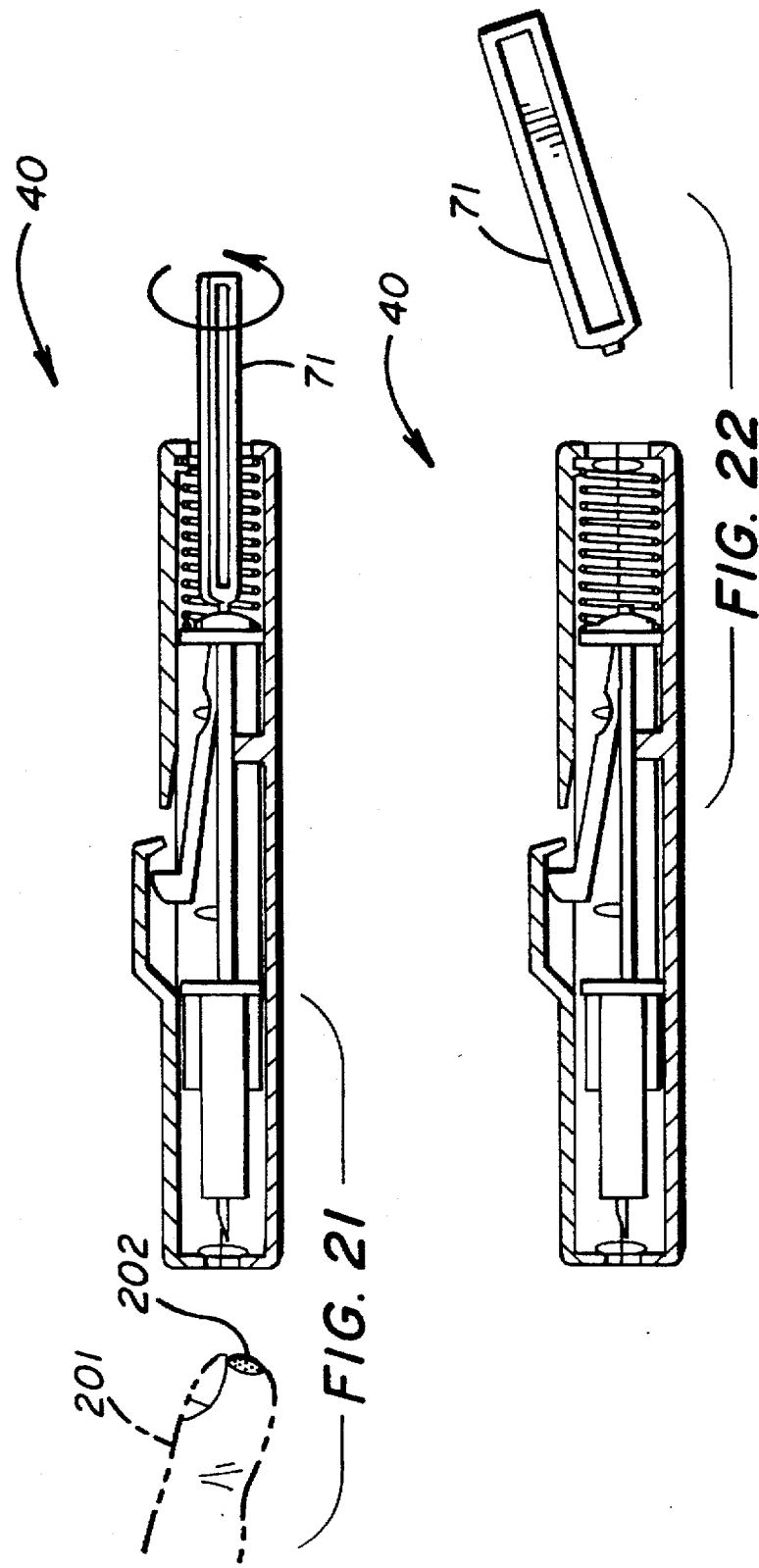

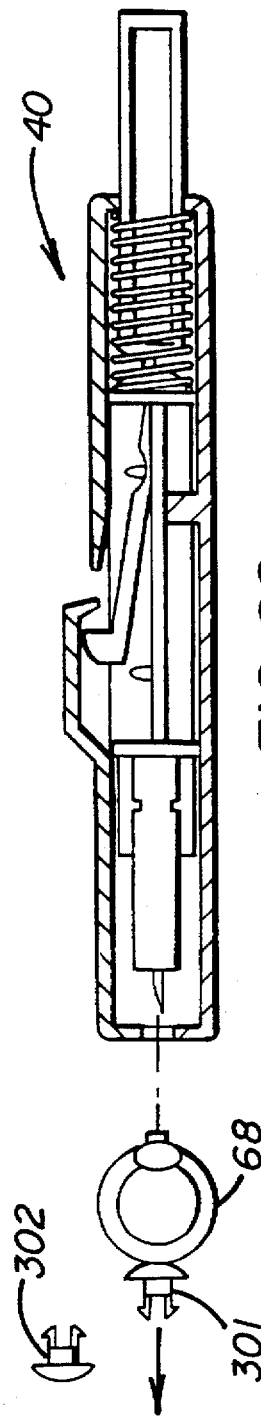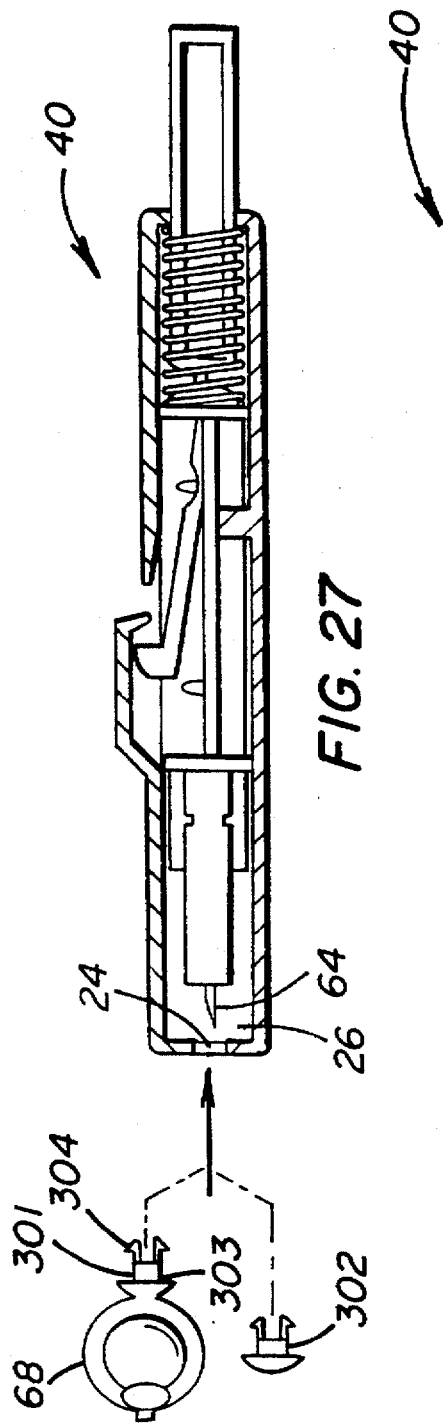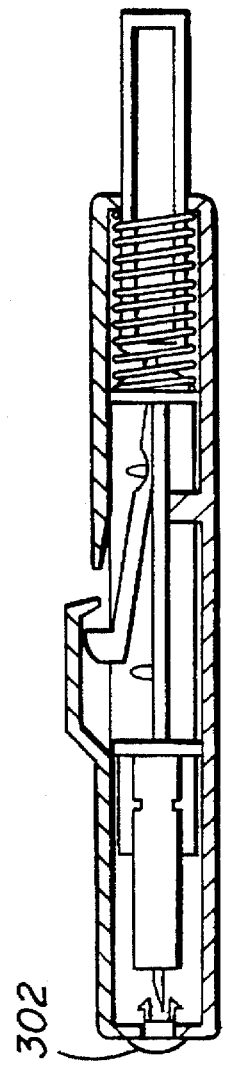

RE-ARMABLE SINGLE-USER SAFETY FINGER STICK DEVICE HAVING RESET FOR MULTIPLE USE BY A SINGLE PATIENT

FIELD OF THE INVENTION

This invention pertains to disposable single-user finger-stick or lancet devices used to initiate bleeding in a patient, and more particularly to disposable single-user lancet devices that involve spring-loaded plunger type lancet tips and that include protective safety features to prevent reuse of a contaminated device by second users but provide a reset feature to permit resetting of a triggered device by a single user.

BACKGROUND

Lancets or other skin incision devices to enable relatively pain free blood sampling from the finger were traditionally designed for multiple use by health professionals, and later for use by diabetics who had a need to make frequent self tests of blood sugar levels. These early devices typically involved a pressure-released spring-loaded device into which a disposable metal lancet tip incased in a plastic housing was placed for each use. The Boehringer-Mannheim Autoclix® is an example of a reusable device of this type. Although the lancet points were relatively inexpensive, the units itself were not, and had to be cleaned between uses.

More recently, it has come to light that cleaning of these reusable devices is often inadequate, and that bacteria or viruses can still be transmitted. The problem is particularly acute in light of the life-threatening nature of infectious agents, including the AIDS virus. This realization has lead to the development of numerous single-unit, disposable devices intended to maintain sterility. These single-unit devices may feature spring-loaded or push-button action, and either reusability or non-reusability. Some devices provide puncture type incisions while others provide a slicing type skin incision. Commercial disposable devices of this type are available from Becton-Dickinson (Microtainer®), Hemochron Tenderfoot™, Owen Mumford (Unistik® and Unistik®2), International Technidyne (Tenderlett™), Palco (EZ-let), and others.

For example, the Owen Mumford (Unistik®) is a single-use non-rearmable spring-loaded device wherein a pull-tab covers the lancet tip and serves to assist the user in arming the lancet. The lancet is armed when the user removes the pull-tab cover, and the pull-tab is necessarily removed to expose the lancet tip before use. If the device is triggered by pressing a release button on its exterior (easily done accidentally while holding the small device) then the lancet tip is propelled forward to pierce the skin when held against the skin, and cannot subsequently be re-armed if the triggering was accidental or for some reason, ineffective in incising the skin. Neither can the Unistik®2 be rearmed and reused by the same user if the amount of blood released from the first incision is insufficient for the test to be conducted.

The Microtainer® is labeled as a single use device; however, its simple plunger mechanism wherein the lancet tip is withdrawn into a housing except when depressed, though effective, can be repeatedly depressed so that the Microtainer® device can be reused repeatedly. It does not provide any protection from transmission of bacteria or viruses that might result from reuse by another person or from accidental cuts resulting from mishandling after disposal. The Hemochron Tenderfoot™ can only be triggered once, and cannot be rearmed in the event of misfire or ineffective incision. There are a variety of other devices that provide similar operating characteristics and similarly lack either safety features or some patient usability.

These conventional devices therefore either provide for multi-use (including reuse when misfired), but do not provide means for permanently disarming the device after use, or they limit use to a single triggering event and thereby help to prevent bacterial and viral contamination, but preclude reuse by the same patient if accidentally triggered or if the single incision does not yield enough blood for the intended test. These limitations are bewildering for the consumer who wants protection, but may be concerned about the costs of devices that through normal handling have become unusable.

They also present a problem for consumer self-test providers as there may be a need to package two or more finger-stick devices with the self-test kit as a means to assure self-test kit usability and adequate blood sample. Heath care providers are concerned because of the ever increasing pressure to reduce costs at all levels. The proliferation of health care providers and consumer self-tests for various medical conditions makes such need even more urgent. Therefore, there is a need for a finger-stick device or lancet that can be rearmed or reset in the event of misfire or ineffective incision, but that can also be permanently disabled after effective use to prevent transmission of bacterial, viral, or other harmful agents to others.

SUMMARY OF THE INVENTION

The subject invention is a lancet or finger stick device operable to make a small incision into the vascular tissue at the finger tip, toe, baby's heel area or other region of a patient from whom a small sample or drop of blood is needed. It provides a single-user finger-stick device having an autologous re-use feature, such that an individual (e.g. a health practitioner or the patient) can reset and reuse the device on the same patient in case of an accidental misfire prior to actual use or if the first incision does not provide a sufficient self-test big sample. The inventive device and method also provide a disabling mechanism which the individual performs immediately prior to disposal of the used device. This combination provides optimum value and protection for the user, and anyone else who may ultimately come in contact with the disabled device.

These features permit the user of a commercial self-test or professional use test to re-stick an individual's fingertip in the event that the first try is inadequate. It also insures sterility of the unused unit and provides enhanced safety since the device cannot be accidentally fired or reused by another individual after being disposed of.

In one embodiment of the invention, the device includes a housing with a hole at one end through which a sharp sterile lancet tip normally enclosed within the housing is able to extend. A lancet support body, also disposed within the housing, supports the lancet tip and is coupled to a resettable force means (such as a spring) in a retracted armed position, which stores energy and upon being triggered, releases the stored energy to move the lancet tip from a protected retracted location inside the housing, through the hole or aperture in the housing a predetermined distance into the patient's finger. The force means also automatically retracts the lancet tip back into the housing immediately after forming the incision. A resettable latch is provided for latching the force means in an energy storing state once armed, and a resettable release means, such as a release or trigger button, is provided for releasing the latch to allow the force means to release the stored energy and thereby to drive the lancet tip outwardly from the housing.

These and other features of the invention will be apparent to those having ordinary skill in the art from the appended description and drawings.

BRIEF DESCRIPTION OF THE DRAWINGS

FIG. 4 is a diagrammatic illustration showing a perspective exterior view of a second embodiment of the inventive finger-stick device shown prior to first use.

FIG. 5 is a diagrammatic illustration of a first end view of device particularly showing the protective cap covering the lancet tip.

FIG. 6 is a diagrammatic illustration of a second end view of the device particularly showing the activating plunger extending from an aperture in the device housing.

FIG. 8 is an illustration showing a plan view of the interior of the upper half housing.

FIG. 9 is an illustration showing a plan view of the interior of the lower half housing.

FIGS. 13a–13e are illustrations of a prior-art lancet suitable for use with the inventive finger-stick device.

FIG. 14 is a diagrammatic illustration showing a partial cut away view of the preferred embodiment of the inventive finger stick device in a pre-use configuration with the protective lancet tip cover still in place.

FIG. 15 is a diagrammatic illustration of the preferred embodiment after removal of the protective lancet tip cover and just prior to device arming.

FIG. 16 is a diagrammatic illustration of the preferred embodiment in the stage of being armed for use.

FIG. 20 is a diagrammatic illustration of the preferred embodiment showing the lancet tip after withdrawal into the housing after skin puncture.

FIG. 21 is a diagrammatic illustration of the preferred embodiment showing the activation plunger being twisted to break the frangible neck and disarm the device.

FIG. 22 is a diagrammatic illustration of the preferred embodiment showing the disarmed device.

FIG. 26 is a diagrammatic illustration of a fourth alternative embodiment of the inventive finger-stick device showing protective non-removable caps for insertion after effective use as a device disarming means.

FIG. 27 is a diagrammatic illustration of the fourth embodiment showing insertion of one of two alternative protective non-removable caps.

FIG. 28 is a diagrammatic illustration of the fourth embodiment showing the device in FIG. 27 after insertion of a non-removable protective cap.

DESCRIPTION OF THE SPECIFIC EMBODIMENT

The subject invention is a lancet or finger stick device operable to make a small incision into the vascular tissue at an appropriate site, e.g. the finger tip, toe, heel of the foot or other similar region of the patient from whom a small sample or drop of blood is needed. For example, in the consumer diagnostic self-test market there are devices, such as blood glucose assay devices, cholesterol assay devices, and the like, that require a small sample of the patient's blood to perform the particular diagnostic test. The sample may generally be one or a few drops of blood.

The subject invention provides a finger-stick device having an autologous re-use feature, such that an individual (for example, a health practitioner or the patient him- or herself) can reset and reuse the device in case of a misfire or if the first incision provides inadequate blood to obtain the required blood sample amount, as well as a disabling mechanism which the individual performs prior to disposal of the used device. This combination provides optimum value and protection for the user, patient or other who may intentionally or accidentally come into contact with the used device.

Figure 1:
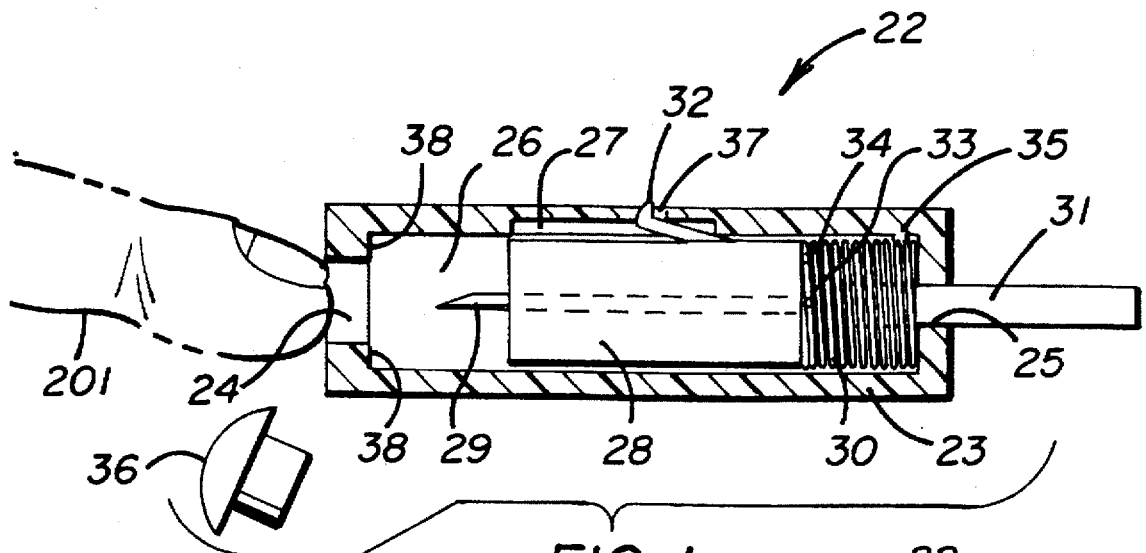
FIG. 1 is a diagrammatic illustration showing a partial cut away perspective view of one embodiment of the inventive finger stick device in the activated or armed configuration ready for use.

For further understanding of the invention, the drawings will now be considered. In FIG. 1 there is shown a simple embodiment of the inventive finger stick device 22. A generally cylindrical outer housing 23 has a first round aperture 24 at a first end and a second round aperture 25 at the opposite end, and defines a cylindrical inner bore 26 having a recessed elongated guide slot 27 therein. A cylindrical lancet body 28 having a diameter slightly smaller than that of inner bore 26 is slidably disposed within bore 26. Lancet tip 29 is preferably stainless steel and is formed integral to and extends from plastic body 28 a predetermined distance. A bias spring 30 which provides the force to drive lancet tip 29 into the patient's skin is fixedly connected to a rear end surface of lancet body 28 opposite to the lance tip and to housing 23 such as with a cupped depression 34 for receiving a coil of spring 30 proximate second aperture 25 with slot 35 formed into the inner surface of housing 23. The spring 30 may also be attached by any other conventional fastening method such as by gluing, molding, and the like. A plunger 31 provides retraction means and is removable from the lance body 28 at frangible or breakable necked region 33 extends from the rear end of the lance body, concentric with and through bias spring 30, and out second aperture 25, where it is accessible to a user's finger grasp. The user pulls the plunger away from the housing to compress spring 30 and thereby load energy into the spring for later release. The housing, lancet support body, latch/release arm and other components may conveniently be fabricated from plastic. The spring and lancet tip are preferably made from metal. Corresponding elements in each figure are the same unless otherwise indicated. Reference numerals have been left off some drawings to more clearly present each embodiment.

A spring loaded latch and latch release button 32 is connected to body 28 and slidably disposed within guide slot 27. Latch and latch release button 32 serves several functions including preventing rotation of lancet body 28 within bore 26, latching the body 28 in an armed condition, and providing a release button for the latch itself as described hereinbelow.

Advantageously a once-removable hard protective cap or seal 36 is disposed proximate the first aperture 24 to protect the user from the sharp lance tip 29 prior to use, to preserve tip sterility, and to serve as an indication that the device is new and has not been used previously.

This embodiment of the finger-stick device 22 has three static states or configurations, and operates through a continuum of dynamic configurations between these static states. During storage and when the protective cap 36 is first removed, the spring 30 is in a relaxed non-compressed, non-extended equilibrium state, and the lance body 28 and integral tip 29 are maintained within the housing and from contact with the cap 36 by the stiffness of bias spring 30.

With reference to FIG. 1 (which shows the device 22 in the armed condition), just prior to use, the inventive device 22 is armed by pulling back on plunger 31 to compress bias spring 30 until spring loaded latch button 32 can extend through a third hole or aperture 37 in housing 23, thereby preventing further rearward retraction and latching the spring 30 in compressed condition. The latch arm 98 is advantageously formed from a stiff elastic material so as to have a spring like quality. The cross sectional area of the arm is adjusted in concert with the material properties to provide the desired latching force. This is the activated or armed static condition of the device.

During use to create an incision in a patient, the device is placed in contact with the patient's finger tip 201 so that when the lance tip extends through the first aperture 24 (described below), it will puncture the skin to a predetermined depth generally between about 0.5 mm and about 5 mm, and more typically between about 1 mm and about 3 mm. Latch button 32 is depressed so that the latch button exits the third aperture 37 into guide slot 27 which originally received and held the latching button or tab 32, thereby releasing the latching button 32 so that the heretofore compressed bias spring 30 is allowed to expand and accelerate the lance body 28 and tip 29 forward toward and through the first aperture 24.

Figure 2:
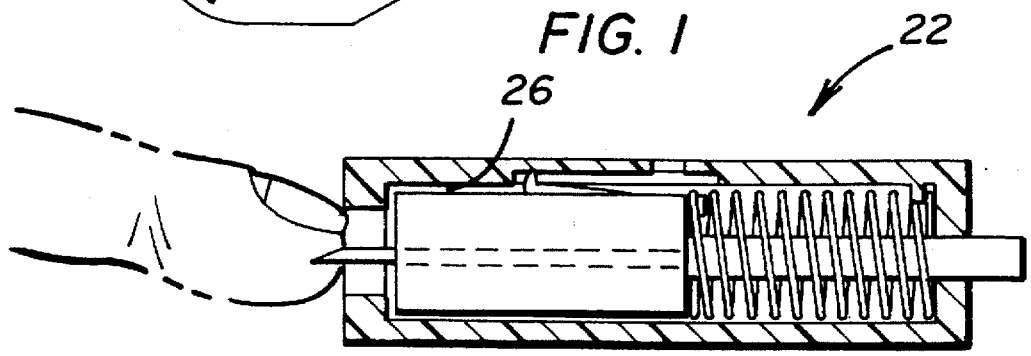
FIG. 2 is a diagrammatic illustration showing a partial cut away perspective view of the embodiment in FIG. 1 during operation at the stage where the lancet tip is fully extended into a patient's finger tip.

Movement of the lance body 28 forward is limited by a movement limit stop 38, here provided by a thickened portion of the housing 23 proximate first aperture 24, which limits the forward movement of lancet body 28. The first aperture 24 (typically round) has a diameter that is smaller than the abutting dimension (e.g. diameter) of the lance body 28 so that the lance body 28 cannot move through aperture 24 beyond the movement limit stop. The thickness of this limit stop 38 is chosen in concert with the length of the lance tip 29 to provide the desired skin puncture depth. FIG. 2 illustrates the condition of device 22 when the lancet tip is at the limit of forward movement into the patient's finger tip.

The length of bias spring 30 is selected such that when the front surface of lance body 28 reaches the stop 38, the bias spring 30 is in an extended condition and therefore immediately contracts, thereby retracting the lancet tip 29 from the patient's finger back into the housing 23.

If the user accidentally misfires the device 22, or does not obtain a satisfactory incision to draw sufficient blood, the device 22 may be reset or reactivated by again pulling the plunger 31 rearward as before, until tab 32 latches into aperture 37, and re-depressing the latch release button. This arming-releasing-rearming can be done multiple times until satisfactory results are obtained.

Figure 3:
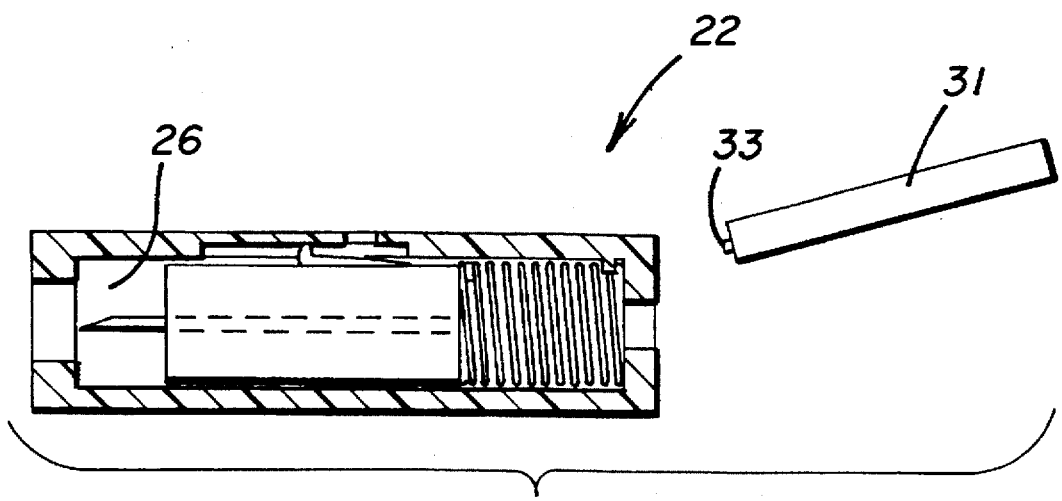
FIG. 3 is a diagrammatic illustration showing a partial cut away perspective view of the embodiment in FIG. 1 after use and deactivation.

As illustrated in FIG. 3, once a satisfactory sample has been obtained, the device is permanently deactivated by breaking the plunger 31 from the remainder of the lancet body. Such breaking is easily accomplished by providing a thin necked coupling 33 between plunger 31 and lancet body 28 that is strong enough to withstand multiple pulls during the one or more activations that a single device 22 may encounter, but that is sufficiently fragile that it may be broken when desired, such as by providing a frangible necked connection 33 between the body 28 and the plunger 31 such that a twisting motion permanently separates the two components.

Figure 7:
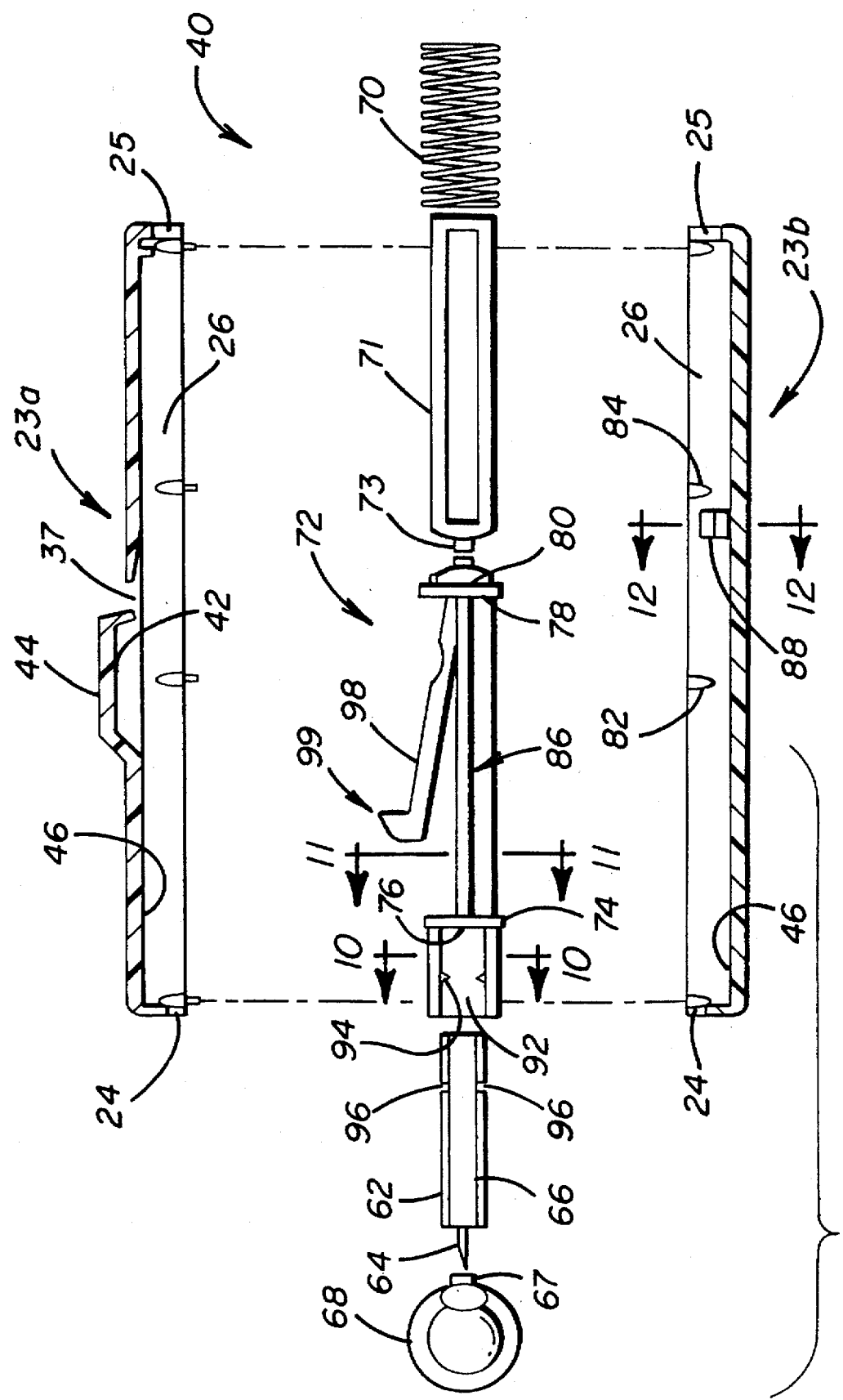
FIG. 7 is a diagrammatic illustration showing an exploded partial cut away perspective view of the preferred embodiment of the inventive finger stick device in FIGS. 4–6.
Figure 12:
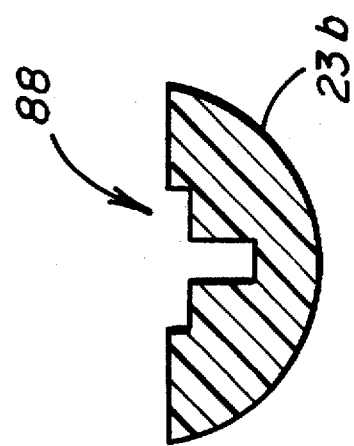
FIG. 12 is an illustration showing a sectional view through region D—D of the lower housing half.
Figure 11:
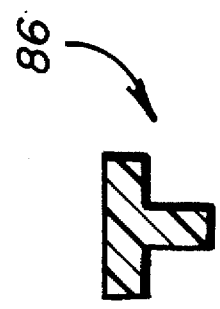
FIG. 11 is an illustration showing a sectional view through region C—C of the trigger assembly.
Figure 10:
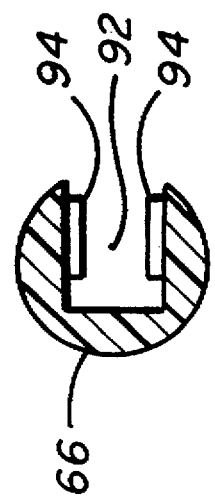
FIG. 10 is an illustration showing a sectional view through region B—B of the trigger assembly.

This simple embodiment having been described, an alternative and preferred embodiment having additional features is now described relative to FIGS. 4–22. In FIG. 4 there is shown an external perspective view of a preferred embodiment of the inventive finger-stick device. FIGS. 5 and 6 show end plan views of the exterior of device 40, and FIG. 7 is an illustration of an exploded partial cut away view of device 40. FIGS. 8 and 9 show internal plan views of upper and lower cover 23a and 23b. With respect to these figures, the device 40 has a tubular outer housing 23, here formed from two pieces (23a, 23b) which surround the internal assembly and provides protection and ease of handling for the device. The housing is conveniently formed in two half pieces such that the assembled components are placed within the interior boundaries of the two pieces, then the two halves are aligned, such as with sets of mating registration pins and sockets, and then connected such as with glue, by welding, with clips, or other conventional fastening methods. While the housing 23 may be any shape and formed of any material, the housing is conveniently in the form of an elongated cylindrical shaped tube fabricated from high impact plastic or polymeric material with first aperture 24 and second aperture 25 provided at opposite ends of the tube shaped housing, and a third aperture 37 provided through the housing medial to the two opposing ends through the cylindrical wall of the housing.

The housing forms a substantially cylindrical inner tube or bore 26 which also advantageously includes a generally elongated rectangular expanded region 27 within the housing cavity and aligned along the cylindrical axis of the housing, and which forms a protuberance 44 on the exterior wall adjacent the third aperture 37. The functionality of these apertures and protuberances are described below. Such cylindrical shape readily provides internal support for the functional components and provides an easily handled and articulated form for the user of the finger-stick device.

The housing forms a symmetrical cylindrical interior chamber 26 having interior wall 46 through which lancet unit 62, trigger assembly 72, and spring 70 are connected to each other and slidably disposed relative to the housing. Axial alignment of trigger assembly 72 and lancet unit 62 which is coupled to trigger assembly 72 within the cylindrical bore 26 is maintained by first cylindrical slider 74 and second cylindrical slider 78 which are sized to slidably fit bore 26. During operation of the device 40, maximum rearward movement (away from first aperture 24) of trigger assembly 72 is limited by abutment of the rear surface 76 of slider 74 with an inwardly protruding first set of stops 82 (82a, 82b). In analogous manner, maximum forward movement (toward first aperture 24) of trigger assembly 72 is limited by abutment of the front surface 80 of slider 78 with an inwardly protruding second set of stops 84 (84a, 84b). Operation of these cylindrical sliders and stops is described in more detail hereinafter. These first and second sets of stops are conveniently provided by upper and lower housing half alignment pins and mating sockets, but separate structures for each function could alternately be provided.

Trigger assembly 72 is preferably formed on a single plastic molded part and includes a T-shaped body portion 86, a lancet tip receiver section 92, sliders 74 and 78, plunger 71 including frangible neck section 73, a spring fastening clip 119 and a latch and release mechanism which includes latch arm 98 and latch/release button 99. (See FIG. 11.) The trigger assembly 72 advantageously includes a T-shaped section 86 that mates to a T-notched region 88 of the housing 23. (See FIG. 12.) The T-shaped section 86 is slidably mated to the T-notched region 88 and prevents rotation of the trigger assembly about the cylindrical axis of the assembly and housing 23. An elongated plunger 71 extends rearward toward and through second aperture 25 to provide means for the user to pull the trigger assembly 72 rearward to compress spring 70 to load energy into the spring. Plunger 71 is connected to the main body of the trigger assembly by a frangible neck section 73 that is strong in tension, so that normal pulling to arm the device does not break the neck section, but can be broken with a deliberate rotational twist. Preventing rotation of the internal components (e.g. the T-shaped body section 86) relative to the housing 23 is advantageous for operation of safety features of the device including initial activation of the device 40 prior to use, and deactivation by breaking off plunger 71 after use prior to disposal as described hereinafter.

Lancet unit 62 comprises a sharp sterile lancet tip 64 of the type intending for plunge incisions of the patient's skin, and a supporting lancet body 66. Lancet unit 62 also advantageously includes a protective cover or cap 68 over tip 64 which is connected to lancet body 66 by a frangible neck region 67. Cap 68 preserves sterility until the cap is removed, prevents accidental cuts or punctures during handling prior to use, and serves as an indication to the user that, when intact, the device has not been used. The frangible neck region 67 is easily broken by twisting cap 68 to thereby expose lancet tip 64. Recall that T-shaped section 84 in combination with T-shaped slot 88 prevents rotation of the internal components relative to body 23. The inventive device 30 provides special operative features, such that when the cap 68 is removed (by safe user movement away from the sharp lancet tip) from the tip 64, the tip 64 is immediately and automatically withdrawn into the housing to prevent contact that could compromise sterility and to prevent accidental cuts or punctures. This feature is described hereinafter relative to FIGS. 14-22. While, various lancet units 62 of the type described may be used, the lancet unit described in U.S. Pat. No. 3,358,689 to Higgins in particular, for example, may be used.

Lancet unit 62 is adapted to fixedly mate to a lancet body receiving notch 92 thereby fixing the position of the lancet tip with respect to the trigger assembly 72 and with respect to the inner and outer surfaces of housing 23 by the nature of operation of cylindrical sliders 74,78 and stop sets 82,84.

Lancet body 66 and receiving notch or cup 92 advantageously provide a snug fit together so that the lancet tip position is properly maintained. Advantageously, one or both of the body 66 and receiving cup 92 include ridges 94 and/or notches 96 such that a positive lock is established between the body and the notch. Alternatively, the receiving cup 92 may include relatively sharp molded ridges that can slice into the somewhat soft polymeric body of lancet unit 62 to thereby fix the location of the body 62 in the notch 92. Of course, the lancet body and lance tip may be formed integral with the body of the trigger assembly 72 such as in a single plastic molding, thereby eliminating the need for separate alignment and assembly. However, the use of conventional commercial lancet tips separate from but attachable to the trigger assembly 72 is preferable because the tips are readily available, are relatively inexpensive because of the large volumes made and sold, and because their use eliminates the need for separate and relatively more expensive sterile production facilities for the other stick-finger device components.

Trigger assembly 72 also includes a latching arm 98 and a latch release button 99, the operation of which will be described hereinafter with reference to FIGS. 14-22. FIGS. 14-22 are partial cut a way diagrammatic illustrations that show the overall operation of the inventive finger-stick device 40 as well as the function of internal components.

With reference to FIG. 14, there is shown a partial cut-a-way view of the inventive device prior to use. The protective cap 68 is still attached to the lancet body 66 via the frangible neck section 67 and serves as a positive indication to a user that the device 40 has not been used and that the lancet tip 64 underlying the cap is sterile. Plunger 71 is in a first start position and has not been pulled rearward. Trigger button 99 is protected under housing protrusion 44 and its absence from view serves as an additional indication that the device has not been activated and is not immediately available to the user to trigger the device.

With reference to FIG. 15, the user has grasped protective cap 68 and while holding housing 23, twisted the cap until the frangible neck section 67 fractures. As the neck section begins to fracture, a slight tension from spring 70 urges the trigger assembly 72 rearward, thereby drawing the lancet tip 64 into housing 23. Because the user's fingers removing the cap 68 and the lancet tip 64 are moving in opposite directions and the lancet tip is never exposed outside of the housing prior to its first use, there is no danger of accidental puncture and little danger of contamination.

As illustrated in FIG. 15, immediately after the cap removal, the plunger 71 automatically retracts rearward slightly, spring 70 is in a relaxed condition (neither extended nor compressed) and trigger release button 99 is still protected under protrusion 44. The trigger button 99 is not visible to the user, thereby providing a visual indication that the device is not armed or ready for immediate use.

With reference to FIG. 16, the user grasps the device between the fingers of one hand, and gently pulls back on plunger 71 until cylindrical slider 78 contacts stops 82. During this pull-back process, latch arm 98 and latch release button 99 are drawn rearward along the inner surface 42 of protrusion 44. The latch arm 98 is advantageously made of a stiff but elastic plastic material and is somewhat compressed by contact with the inner surface 42 of protrusion 44 so that upon reaching the rear wall section 105 of protrusion 44, the latch release button is directed temporarily inward toward the center of the housing so as to pass under the restricting lip 106, and then upon continuing its rearward travel, immediately springs back outward upon encountering third aperture 37 which it is sized to easily fit. The position at which the trigger button springs into third aperture 37 corresponds approximately to the location at which stops 82 limit rearward movement of the trigger assembly.

Latches/release button 99 is advantageously shaped with a tapered upper surface 107 so as to be easily guided along the protrusion 42, under the lip 105, and through aperture 37 on pull-back (and upon subsequent release); and a flat frontal surface 108 which abuts a similarly flat mating surface 112 on the exterior surface of protrusion 44, thereby latching and maintaining the trigger assembly in a rearward and activated condition as illustrated in FIG. 16. The trigger release button 99 is now visible and accessible to the user and serves as a visual indication that the device 40 is armed and ready for immediate use.

Figure 17:
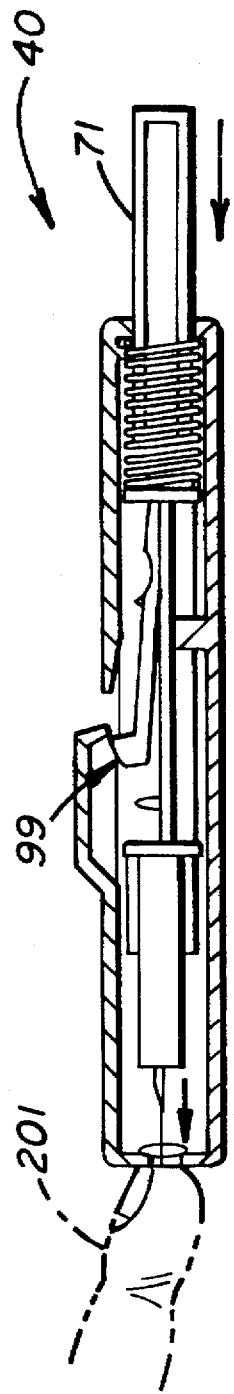
FIG. 17 is a diagrammatic illustration of the preferred embodiment showing the lancet tip moving forward to puncture the patient's skin.
Figure 18:
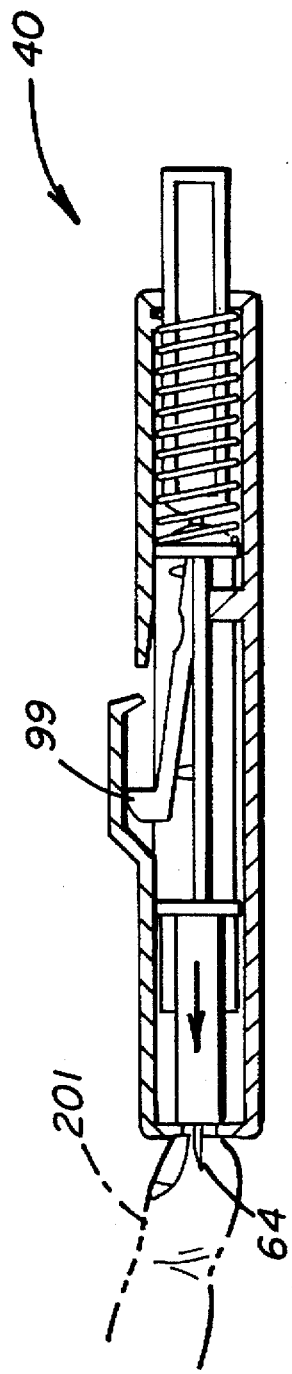
FIG. 18 is a diagrammatic illustration of the preferred embodiment showing the lancet tip at maximum penetration.
Figure 19:
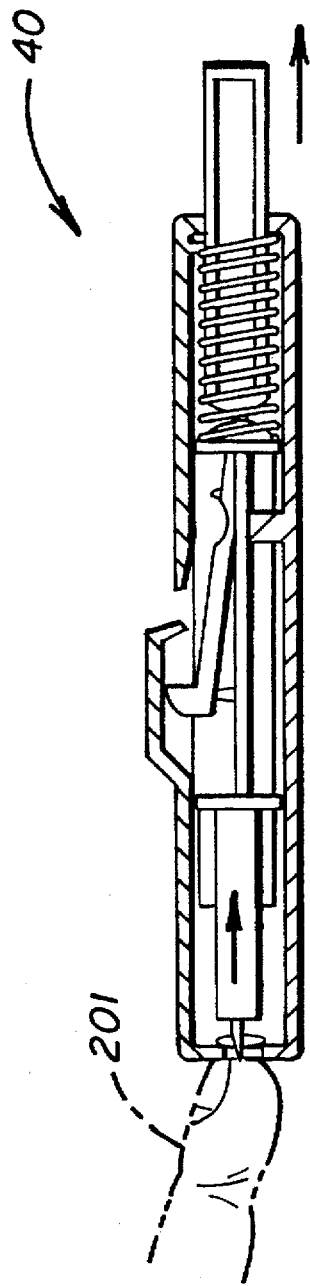
FIG. 19 is a diagrammatic illustration of the preferred embodiment showing the lancet tip being automatically withdrawn into the housing after puncture.

FIG. 17 is a diagrammatic illustration of the finger-stick device just after pressing trigger button 99 to release the trigger mechanism. Prior to release, the user places the housing adjacent the first aperture 24 in contact with the patients finger 201 (or other similar skin tissue area). Aperture 24 is advantageously sized small enough so that even with excessive pressure, the amount of patents flesh that extends into the housing cavity 26 is limited, thereby assisting in limiting the depth of lancet tip penetration. Aperture 24 is also advantageously sized with an aperture diameter smaller than that of lancet body 66 so that the lancet tip 64 excursion outside of the housing 23 is by its size limited.

FIGS. 17–20 show successive operational stages after release of trigger button 99. In FIG. 17, trigger button 99 is slightly depressed, so that the flat portion 108 is moved away from abutting contact with flat housing wall portion 105. The elastic spring-like characteristic of trigger arm 98 and the tapered shape of tapered surface 106 readily permits movement of the button 99 under the lip of the housing so that acceleration forward of the trigger assembly by the energy previously stored in spring 70 during pull-back, is not unduly restrained. Movement of the trigger assembly 72 continues forward so that lancet tip 64 exits aperture 24 to puncture the patient's skin until cylindrical slider 74 contacts stops 84 or the front of lancet body 66 contacts the inside of the front wall 122 of body 23 to limit any further movement forward. Either stops 84 or inner front wall 122 are alone sufficient to limit movement of the lancet tip.

By selecting the location of the limit stops 84 or the thickness of front wall 122 of housing 23 and the dimensions of the lancet unit including the dimension (particularly the length) of the lancet tip 64, the penetration depth of the lancet may be easily and precisely regulated so as to reach the capillarid vasculature of the patient but without excessive penetration that might cause undue pain, excessive bleeding or bruising. In an exemplary embodiment of the invention, the lancet tip 64 extends between about 1 millimeter and about 4 millimeters from the lancet body and, typically extends between about 0.5 millimeters and about 3.5 millimeters, from the exterior surface of the housing through aperture 24. The patient's skin typically extends somewhat into aperture 24 during operation of the device. Different devices having different lancet lip 64 extensions from the housing may be provided for various applications. For example, a shorter tip extension than the tip extension used with adults may be provided for use with children and infants. And, different tip lengths (and/or tip diameters) may be provided for use on different parts of the patient's body, for example the finger, toe, baby's heel region, and the like. Lancet tips may be made from stainless steel wire with a short sharp tapered tip for cutting. Lancet tip lengths of between about 1 mm and about 5 mm are generally used, and have diameters between about 0.02 and about 2 mm, more typically between about 0.6 mm and about 1.2 min. The lancets available from Sherwood Medical of St. Louis, Mo. may, for example, be used with the inventive device and, are available with lancet tip length and diameters about as follows: 0.125 inches×0.031 inches diameter (Model M602), 0.089 inches×0.041 inches diameter (Model O.P.D.), and 0.071 inches×0.031 inches diameter (Model NEOLET). Of course, those workers having ordinary skill in the art in light of this disclosure will appreciate that the characteristics of the cupped lancet body receiving region 92 will be designed and fabricated in conjunction with the characteristics of the lancet body to be held by that receiving region.

Recall that spring 70 has a relaxed length such that when relaxed (neither compressed nor extended), lance tip 64 is contained entirely within housing 23. Therefore, when trigger assembly 72 reaches the maximum forward position such that spring 70 is in an extended condition, it stops momentarily as described, but is immediately pulled back rearward by the extended spring toward the second aperture 25. Although in principle, the spring 70 might oscillate forward and rearward until all energy has been absorbed, in practice, the energy absorbed during skin puncture, by the spring itself, and though sliding friction of components of the device severely limit oscillation such that the lance tip exits the aperture 24 only once for each activation and release. The trigger assembly settles back to its equilibrium condition as shown in FIG. 20, which is the same configuration shown after removal of the protective cap in FIG. 15.

If the first use of the device 40 as described is successful, for example, if the device was not accidentally fired and was not fired without sufficient contact with the finger tip to cause blood flow, then the device is deactivated as shown in reference to FIGS. 21–22. The user grasps the device between the fingers of one hand (recall that the lancet tip is protected inside the housing after use) and the plunger 71 is twisted around an axis aligned with the axis of the cylindrical housing to break the frangible neck section 73 connecting the plunger 71 with the main body of trigger assembly 72. Once the plunger 71 has been broken away in this manner, reinsertion of the plunger is ineffective, and the device 40 can no longer be activated or used.

However, if the device has been accidentally triggered, and has not otherwise been contaminated, then the plunger 71 may be used a second time (or repeatedly) until use is effective to obtain an adequate blood sample as described relative to FIGS. 14–20 above. It is intended that a first incision into a single patient does not contaminate the lancet tip for a second use on the same patient within the same test session period. It will readily be appreciated that the breakaway plunger structure permits multiple reset activations of the device, and then at the user's option and control, means for easily and permanently disabling the device. Provision of the protective cap provides assurances that in spite of the ability to rearm the device after a misfire, a used and reactivated device cannot be confused with a new device.

Figure 23:
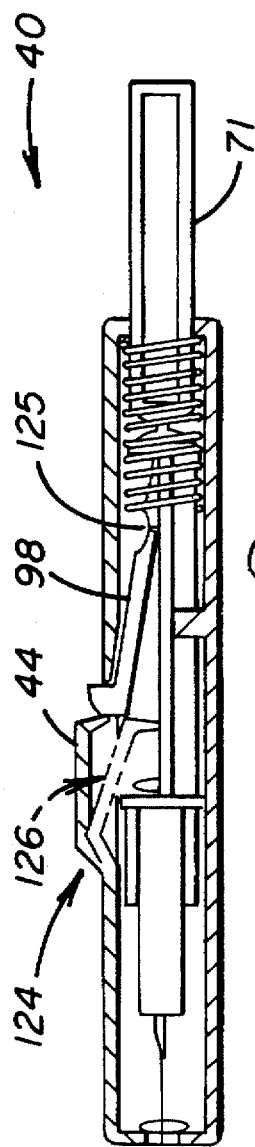
FIG. 23 is a diagrammatic illustration of a third alternative embodiment of the inventive finger-stick device showing a break-away latch trigger as a disarming means.
Figure 24:
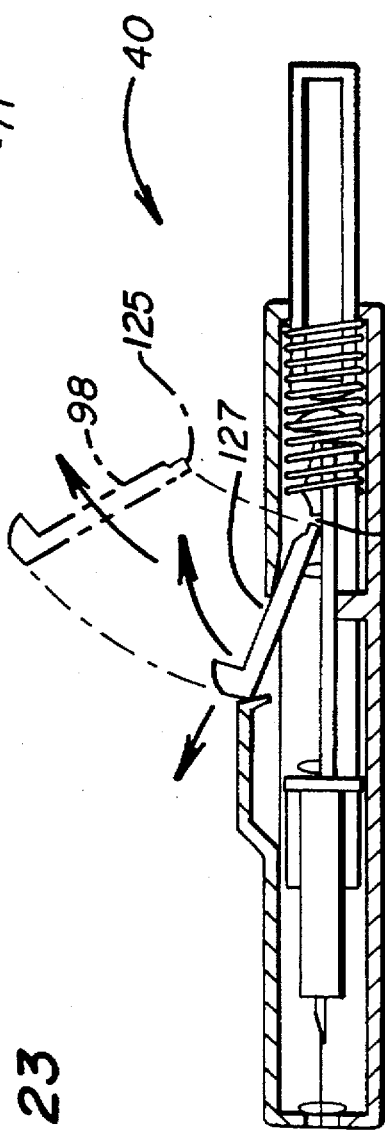
FIG. 24 is a diagrammatic illustration of the third embodiment of the device showing an exemplary pull and twist removal of the break-away latch trigger.
Figure 25:
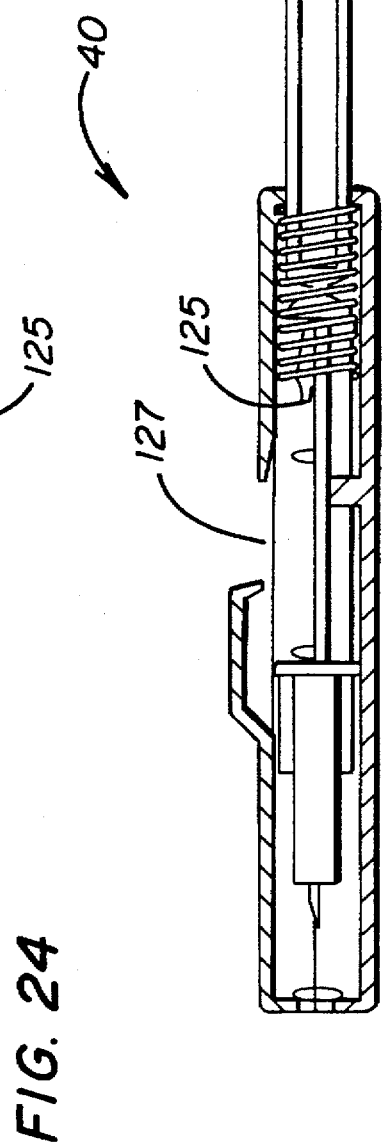
FIG. 25 is a diagrammatic illustration of the third embodiment of the device showing the disarmed device with the break-away latch/trigger arm removed.

A third alternative embodiment is now described with respect to FIGS. 23–25 which show an embodiment of the invention having features similar to those already described except that the latch/release arm 98 is provided with a break-away region 125 such that after effective use of the device, the latch/release arm 98 is broken away at that break-away point to remove the arm and thereby to permanently deactivate the device. In order to break away the arm 98, it is advantageous to provide access to the button 99 and/or arm 98 so that it may be grasped with the fingers (or alternatively with a grasping tool) and pulled and/or twisted from its point of attachment at break-away region 125. The break-away region may be provided by a thinned-frangible neck region, by notches, or by other means that assist in concentrating the user's twisting forces to break the arm away. Access to the latch/release arm 98 is provided either by providing the housing protuberance 44 with a flexible pivot region so that pressing down on the protuberance 44 at location 126 provides access to grasp the arm 98, or alternatively to provide a somewhat larger aperture 127 than that provided by aperture 37 of the first embodiment, so that the arm 98 may be graphed by the fingertips of a user and twisted to break and remove. A deactivated device incorporating the larger aperture 127 and showing the latch/release arm 98 removed is illustrated in FIG. 25.

A fourth embodiment of the invention is illustrated in FIGS. 26–28. Two types of protective caps 301,302 may alternatively be provided. A first protective cap is formed integral to the lancet tip cover 68. A second alternative cap 302 is separate from the lancet cover 68. Both alternative caps include the same features for deactivating and permanently disabling the device. Prior to use, the protective cap 301 (integral with lancet tip cover 68) covers the first aperture 24 of the finger stick device to prevent accidental cuts and to preserve the sterility of the lancet tip 64. However, after effective use of the device for one or more incisions by the same individual, the user replaces the protective cap 301 in a reversed (180 degree rotated) orientation such that barbs 304 integral to the cap 301 compress inwardly to pass through aperture 24, but then expand and latch to the interior of the housing such that the cap cannot be removed by the user. Alternatively, a second protective cap 302 could be provided in addition to the protective lance tip cap 68 for insertion after use of the device. Both caps 301 and 302 include compressible barbs 304. Insertion of the non-removable cap 301 or 302 disables the device and prevents further use.

Both caps 301 and 302 are insertable into the lancet tip exit aperture 24 and deactivation of the device is accomplished by inserting the cap or cover 301 or 302 into the lancet tip exit aperture 24 to prevent passage of the lancet tip through the lancet tip exit aperture. The cover 301 and 302 includes a cover body 303 portion and pliant cover barbs 304 connected to the cover body. The pliant cover barbs 304 have a dimension larger than the lance tip exit aperture 24 but are advantageously tapered so that insertion of the barbed portion 304 into the aperture 24 compresses the barbs inwardly thereby temporarily reducing the diameter of the cover until the barbs pass through the aperture into the larger cavity or bore 26 of the housing. Upon passing through the aperture 24, the barbs expand outwardly into the housing bore 26 and the flat portions of the barbs prevent the cover 301,302 from being removed. FIG. 26 illustrates the device prior to use upon removal of the lancet tip cover 68 having integrally formed protective post-use cover 301. FIG. 27 illustrates the manner in which a reversed cover 301 or a separate cover 302 is inserted into aperture 24 to deactivate the device. FIG. 28 shows the fourth embodiment of the inventive finger-stick device in a deactivated state with the one-way insertable cap 302 installed in the aperture 24.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A finger stick device for producing a plunge incision into the skin of a patient; said device comprising:

a housing having a first aperture;

a sharp lancet tip initially disposed within said housing;

a lancet support body disposed within said housing and connected to said lancet tip for supporting said lancet tip;

resettable force means coupled to said support body for storing energy and for releasing said stored energy to linearly move said lancet tip from a location inside said housing through said first aperture to a predetermined location outside of said housing;

resettable latch means for latching said force means in an energy storing state; and resettable release means for releasing said latch means to allow said force means to release said stored energy to drive said lancet tip outwardly from said housing wherein said resettable force means and resettable release means make up an autologous re-use feature, such that the finger stick device can be reset for use on the same patient in the event of an accidental release of stored energy producing linear movement of the lancet tip outwardly from the housing or in the event that a supplemental plunge incision is desired on the same patient, and a disabling means adapted to permanently disable the finger stick device comprising a plunger connected to said support body by a frangible neck section, said frangible neck adapted to be broken by rotation of said plunger relative to said support body, wherein said rotation of the plunger is not automatic or coincident with the movement of the lancet through the aperture the retraction of the lancet and can be voluntarily and manually performed.

2. The device in claim 1, wherein said device further comprises a protective cover disposed proximate said first aperture to prevent access to said sharp lancet tip from outside of said housing.

3. The device in claim 1, wherein said force means comprises an elastic member.

4. The device in claim 1, wherein said force means comprises a spring having a first end fixedly connected to said support body and a second end fixedly connected to said housing.

5. The device in claim 4, wherein said housing comprises a molded plastic elongated cylinder, said first aperture is defined at a first end of said cylinder and said housing defines a second aperture at an opposite end of said cylinder, said device further comprising:

a plunger removably coupled at a first end to said support body by a frangible coupling and extending through said second aperture to the outside of said housing;

whereby movement of said plunger in a first direction by an external agent stores energy in said spring.

6. The device in claim 5, wherein said resettable latch means for latching said force means in an energy storing state comprises an extensible probe and a receptacle for receiving said extensible probe, said extensible probe connected to said lancet support body and moving with said support body in response to movement of said plunger, said extensible probe freely extending into said receptacle when said probe is position coincident with said receptacle, movement of said plunger in said first direction resulting in position coincidence between said probe and said receptacle.

7. The device in claim 6, wherein said resettable release means for releasing said latch means to allow said force means to release said stored energy to drive said lancet tip outwardly from said housing, comprises a trigger button disposed external to said housing and extending into abutting contact with said probe and operative to dislodge said probe from said receptacle, thereby releasing said latch means.

8. A finger stick assembly comprising:
   a hollow housing having a first aperture at one end and a second aperture at an opposite end;
   a lancet unit having a sharp lancet tip slidably disposed near said first aperture and a lancet body enclosed and supported by said housing, and supporting said tip and extending from said tip toward said second aperture;
   a spring coupled to said lancet body and disposed within said housing;
   means for coupling energy into said spring to alter said spring from a relaxed condition to an activated condition;
   latch means for latching said spring in said activated condition;
   release means for releasing said spring from said activated condition; and
   disabling means for permanently disabling said finger stick assembly from moving said lancet tip forward.

9. A re-armable automatically retractable penetrating finger stick assembly, comprising:
   a hollow tubular housing having a first aperture at one end of said housing, a second aperture at an opposite end of said housing, and a third aperture along a wall of said housing;
   a spring having a first end fixedly attached to the interior of said housing proximate said second aperture and having a spring second end;
   a longitudinally slidable lancet support mounted within said housing, fixedly attached to said spring second end, and extending toward said first aperture, said lancet support including means for mounting a lancet unit to said support;
   a lancet unit comprising a sterile lancet tip, and a lancet body;
   a plunger coupled to said support and extending through said second aperture;
   resettable latch means for releasably holding said spring in a compressed condition and said support in a rearward retracted position when said plunger is pulled rearward; and
   resettable release means for releasing said latch means;
   whereby when said latch means is released said compressed spring is allowed to extend to a relaxed position thereby accelerating the combination of said support, said lancet unit, and said spring, forwardly toward said first aperture; the momentum possessed by said combination resulting in movement of said combination beyond an equilibrium position for said spring so that said lancet tip momentarily extends through said first aperture but is pulled back into said housing;
   said plunger being coupled to said support by a frangible neck section, said frangible neck adapted to be broken by rotation of said plunger relative to said support wherein said resettable force means and resettable release means make up an autologous re-use feature, such that the finger stick device can be reset for use on the same patient in the event of an accidental release of stored energy producing linear movement of the lancet tip outwardly from the housing or in the event that a supplemental plunge incision is desired on the same patient,
   and wherein said rotation of the plunger is not automatic or coincident with the movement of the lancet through the aperture the retraction of the lancet and can be voluntarily and manually performed.

10. The device in claim 9, wherein said lancet unit further comprises a protective cover disposed over said lancet tip, and wherein said protective cover is connected to said lancet body proximate said lancet tip by a frangible neck section coaxial with said lancet tip.

11. The device in claim 9, wherein said lancet body is coextensive and integral to said lancet support.

12. The device in claim 9, wherein said lancet body is mounted to said lancet support means by mechanical coupling.

13. A re-armable retractable-lancet finger-stick device, comprising:
   a housing having a lancet tip exit aperture at a first end, a second aperture at an opposite end, and a third aperture;
   a spring disposed within said housing and having first and second ends, said first end fixedly attached to said housing, said spring being movable between an extended state, a relaxed state, and a compressed state;
   a lancet tip supported by a lancet support body slidably disposed within said housing, said support body fixedly attached to said spring second end;
   retracting means for moving said support body from a first location to a second location and for placing said spring in said activated state;
   resettable latch-release means for engaging a latch-release probe into said third aperture to latch said spring in said activated state and for releasing said probe from said third aperture to allow said spring to transition from said activated state through said relaxed state and to an extended state before returning to said relaxed state; and
   wherein said resettable latch-release means is an autologous re-use feature, such that the finger stick device can be reset for use on the same patient in the event of an accidental release of stored energy producing linear movement of the lancet tip outwardly from the housing or in the event that a supplemental plunge incision is desired on the same patient,
   disabling means for permanently disabling said finger stick device and comprising a plunger connected to said support body by a frangible neck section, said frangible neck adapted to be broken by rotation of said plunger relative to said support body,
   wherein said rotation of the plunger is not automatic or coincident with the movement of the lancet through the aperture the retraction of the lancet and can be voluntarily and manually performed.

14. The device in claim 13, wherein said disabling means comprises means for disabling said retracting means to prevent placing said spring in said activated condition.

15. The device in claim 14, wherein said disabling means further comprises a plunger connected to said support body by a frangible neck section, said frangible neck adapted to be broken by rotation of said plunger relative to said support body.

16. A method for providing a blood sample comprising the steps of:

provinding an apparatus including a housing having a lancet tip exit aperture at a first end, a second aperture at an opposite end, and a third aperture; a spring disposed within said housing and having first and second ends, said first end fixedly attached to said housing, said spring being movable between an extended state, a relaxed state, and a compressed state; a lancet tip supported by a lancet support body slidably disposed within said housing, said support body fixedly attached to said spring second end; retracting means for moving said support body from a first location to a second location and for placing said spring in said activated state; latch-release means for engaging a latch-release probe into said third aperture to latch said spring in said activated state and for releasing said probe from said third aperture to allow said spring to transition from said activated state through said relaxed state and to an extended state before returning to said relaxed state; and disabling means for permanently disabling said device;

arming said device using said retracting means to place said device in an activated condition a first time;

latching said device in said activated condition a first time;

releasing said device to propel said lancet tip forward through said exit aperture a first time;

rearming said device using said retracting means to again place said device in an activated condition a second time;

relatching said device in said activated condition a second time;

releasing said device to propel said lancet tip forward through said exit aperture a second time; and manually rotating the plunger relative to the support enough to break the frangible neck section of the plunger and thus permanently deactivating said device so that one of said arming, latching, and releasing operations is prevented.

17. The method in claim 16, wherein said device further includes a activation plunger connected to said lancet support, and wherein step of permanently deactivating said device comprises the steps of:

breaking said activation plunger from said device to prevent further activation of said device.

18. The method in claim 17, wherein said activation plunger is connected to said lancet support by an frangible neck section, and wherein said step of breaking said activation plunger from said device comprises rotationally twisting said activation plunger about the axis of said frangible neck section to break said frangible neck section and sever said plunger from said lancet support.

* * * * *